United States Patent [19]

Bryan et al.

[11] Patent Number: 5,203,203
[45] Date of Patent: Apr. 20, 1993

[54] VISCOMETER FOR IN SITU MONITORING

[76] Inventors: William L. Bryan, 6806 N. Aycliffe Dr., Peoria, Ill. 61614; James M. Bryan, 630 S. Hermitage, Apt. 802, Chicago, Ill. 60612

[21] Appl. No.: 594,950

[22] Filed: Oct. 10, 1990

[51] Int. Cl.[5] ............................................. G01N 11/12
[52] U.S. Cl. ................................................. 73/54.19
[58] Field of Search ....................... 73/57, 448, 861.57; 29/898.069, 899; 384/492

[56] References Cited

U.S. PATENT DOCUMENTS

| | | | |
|---|---|---|---|
| 3,492,120 | 1/1970 | Haller | 29/898.069 X |
| 3,888,113 | 6/1975 | Miranda | 73/57 X |
| 3,953,013 | 4/1976 | Griffith et al. | 29/559 X |
| 4,388,823 | 6/1983 | Garnaud et al. | 73/57 |
| 4,852,388 | 8/1989 | Park et al. | 73/57 X |

FOREIGN PATENT DOCUMENTS

| | | | |
|---|---|---|---|
| 1142067 | 1/1963 | Fed. Rep. of Germany | 73/861.57 |
| 60-78110 | 2/1985 | Japan | |

OTHER PUBLICATIONS

"On the resistance to the Uniform Motion of a Solid Through a Viscous Liquid" Raymond B. Block, Journal of Applied Physics, Oct. 1940, vol. 11, pp. 635-642.
"A Falling Ball Apparatus to Measure Filament Cross--Linking" Thomas D. Pollard Methods in Cell Biology; 1982, vol. 24, pp. 301-311.
The rolling ball viscometer: "An automated way to monitor assembly states of biopolymers" Steven M. Block and Annamma Spudich; American Biotechnology.
Laboratory (ISSN 0749-3223); Mar./Apr. 1987; vol. 5, No. 2, pp. 38-46 "Viscosity and Flow Measurement" J. R. Van Wazer, J. W. Lyonsm; K. Y. Kim, and R. E. Colwell; Viscosity and Flow Measurement/A Laboratory Handbook of Rheology 1963; pp. 272-281.
"The Rolling Ball Viscometer" Robert M. Hubbard and George Granger Brown vol. 15, No. 5, pp. 212-218.
"Small-volume, inclined, falling-ball viscometer" R. H. Geils and R. C. Keezer Rev. Sci. Instrum., Jul. 1977, vol. 48, No. 7, pp. 783-785.
"Viscosity of Organic Liquids at Elevated Temperatures and Corresponding Vapour Pressures" M. S. Medani and M. A. Hasan; The Canadian Journal of Chemical Engineering; Apr. 1977; vol. 55; pp. 203-209.
"A Simple Electronic Capillary Microviscometer" Francisco J. Muller and Julio C. Pita; Analytical Biochemistry 135.
"A Monograph of Viscometry" Guy Barr; Property of Bureau of Agricultural Chemistry and Engineering; Northern Region Research Laboratory; Peoria, Ill. 1931 pp. 259 and 260.
"AMV 200-Automatic Microviscometer . . . for the Rapid and Accurate Determination of the Viscous Properties of Newtonian and Non-Newtonia Fluids." Anton Paar K. G. A-8054 Graz, Postfach 58, Kaemtner Strasse 322; Austria, Europe.
"Viscometers" Cole-Parmer Instrument Company, Chicago, Il. 60648, 1988; pp. 1009-1012 and p. 1.

*Primary Examiner*—Hezron E. Williams
*Assistant Examiner*—Joseph W. Roskos
*Attorney, Agent, or Firm*—Sixbey, Friedman, Leedom & Ferguson

[57] ABSTRACT

An apparatus for measuring in situ the viscosity of a fluid in a sealed container which includes a spherical ball forming an integral package before any fluid is placed within the container. The apparatus further includes a composite ball consisting of a spherical core of one material surrounded by one or more layers of different materials distributed spherically about the core. The container may also be supported by an angular support member which angularly positions the container such that the ball will move within the container through the fluid at a specific speed. A sensing device is provided along the wall of the container to measure the speed of the ball wherein the sensing device includes a pair of sensors spaced apart by a known distance to sense when the ball passes by each of the sensors providing a speed which is useful for calculating the viscosity of the fluid.

16 Claims, 4 Drawing Sheets

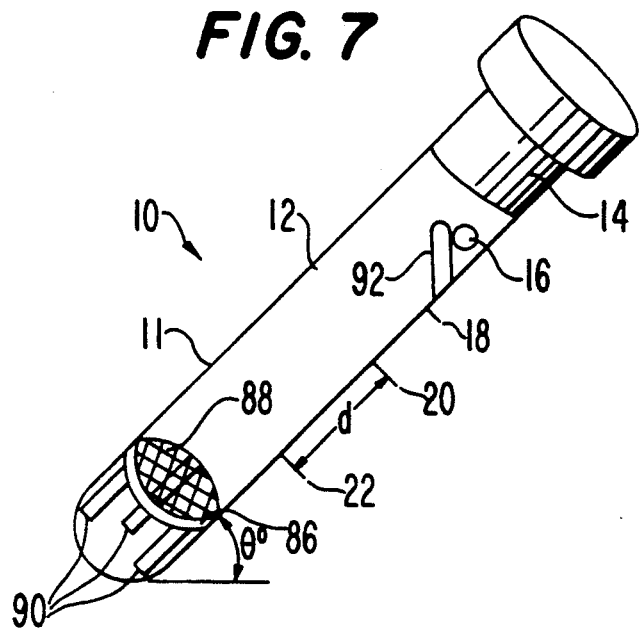
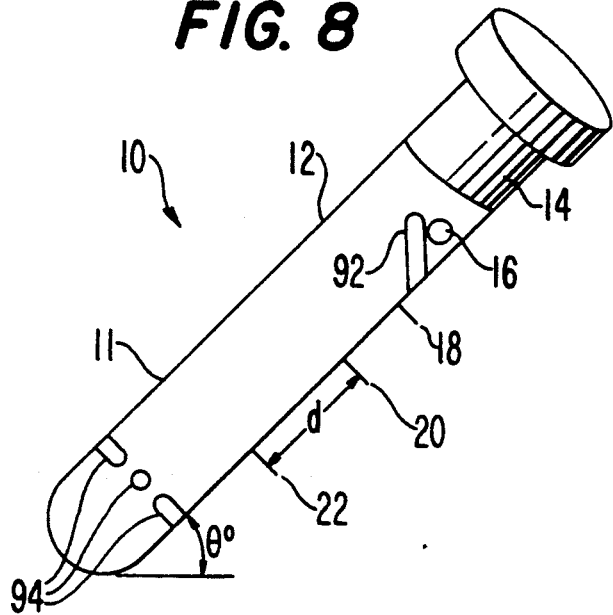

VISCOMETER FOR IN SITU MONITORING

BACKGROUND OF THE INVENTION

1. Technical Field of the Invention

This invention relates to an apparatus for measuring in situ the viscosity of a fluid. More particularly, the present invention relates to an apparatus which allows the measurement of a useful parameter for measuring the viscosity of a fluid held within a sealed laboratory container wherein the measurement can be obtained without disturbing the fluid held therein.

2. Description of the Prior Art

The viscosity of a fluid is a measure of its "flow thickness." Viscosity measuring instruments include falling sphere viscometers (FSV) and rolling sphere viscometers (RSV) based on the Stoke's Law principle, as described in *The Kirk-Othmer Encyclopedia of Chemical Technology*, 3rd Edition, Vol. 20, p. 299-300 (John Wiley 1982). Briefly, Stoke's Law relates the viscosity of a Newtonian fluid to the velocity of a falling sphere. When a sphere is allowed to fall freely within a fluid, it accelerates until the viscous force exactly balances the gravitational force. The Stokes equation for determining viscosity of a fluid using a falling sphere is:

$$\eta = \frac{2r^2 g(d_s - d_l)}{9v} \qquad \text{Equation 1}$$

where r is the radius of the sphere, $d_s$ and $d_l$ are the density of the sphere and the liquid, respectively, g is the gravitational force, and v is the velocity of the sphere. Falling sphere viscometers are generally limited to Newtonian fluids, although they are excellent instruments for routine monitoring of relative viscosities of various fluids.

A generalized form of the Stokes equation for a rolling sphere wherein the sphere rolls down the wall of a cylindrical tube is:

$$\eta = \frac{k(d_s - d_l)}{v} \qquad \text{Equation 2}$$

where v is the translational velocity of the rolling sphere and k is the instrument constant, which is determined by calibration with standard fluids.

In equations (1) and (2), v is the terminal velocity after the sphere has accelerated to maximum velocity, which is determined by measuring the elapsed time, t, for the sphere to fall or roll between two points separated by a known distance d. Assuming that the terminal velocity had been reached at the first point, v=d/t. For a FSV or RSV to be compact or about the size of typical laboratory instruments, it is necessary that v be relatively low such that an excessive initial fall or roll distance is not needed for the sphere to accelerate to v; and an excessive distance between the two measuring points is not required for the elapsed time to be measured accurately.

A viscosity measurement of a fluid with flow thickness similar to that of water by use of a laboratory size container would be very difficult to obtain using FSV or RSV as currently designed having spheres of glass or metal unless the sphere diameter was designed to be very small. Such a design would, however, produce handling problems and require extremely sensitive methods to detect the presence of the sphere at the two measuring points, described above, to reach desired accuracy.

Several types of rotational viscometers are well known, such as described in *Viscosity and Flow Measurement, A Laboratory Handbook of Rheology*, by J. R. Van Wazer, J. W. Lyons, K. Y. Kim and R. E. Colwell, Interscience Publishers (John Wiley & Sons, New York, 1963). In these models, the rotating member of desired geometric shape, which is essentially symmetrical, is mounted on a shaft and connected to the measuring instrument, usually positioned above the liquid to be measured. The rotating member is immersed in the liquid and operated at several constant speeds or rates of rotation. At each speed, the torque required to rotate the member at that rate is also measured. A measure of viscosity of the liquid may be calculated from the torque and the speed by appropriate mathematical relations, or the instrument can be calibrated by measuring the torque and speed of rotation for a number of liquids of known viscosity. The rotating member is usually in the shape of a disc, cylinder, cone, or sphere or some other symmetrical shape such as an inverted cup.

A significant problem exists for the FSV and RSV as well as for the rotating viscometers described immediately above. These instruments require that a sample be removed from a larger supply of the fluid to be tested which is contained in a separate container. This requires that the fluid be exposed to the atmosphere and often sophisticated equipment must be used to keep the sample from becoming contaminated since some fluids such as blood may undergo additional tests which require it to remain sterile. Therefore, a system is needed which facilitates a measurement of the viscosity of a fluid held in a laboratory container without the removal of the fluid therefrom.

Moreover, a spherical ball useful in RSV or FSV systems is needed which has a sufficient diameter to be detected by conventional sensing instruments but which is not too dense so that it can be used in conventional laboratory containers. Glass or metal balls, if shipped in a frangible laboratory container, would be likely to shatter the container during shipment unless they were formed to be extremely small and therefore difficult to detect.

SUMMARY OF THE INVENTION

It is a primary object of the present invention to provide an apparatus for measuring the viscosity of a fluid held within a sealed container which overcomes the deficiencies of the prior art.

Another object of the present invention is to provide a viscometer for obtaining a measurement in situ which is useful in calculating the viscosity of a fluid held within a sealed container without disturbing the fluid held therein.

Yet another object of the present invention is to provide a viscometer for obtaining a measurement in situ in a laboratory container which is useful in calculating the viscosity of a fluid and which includes a sealed container, a spherical ball, an angular support for positioning the container to cause displacement of the spherical ball within the container and sensors located within the range of displacement of the spherical ball wherein the spherical ball is provided within the container as an integral package before the fluid is placed therein.

Still another object of the present invention is to provide a transparent, frangible laboratory container for obtaining a measurement in situ useful for calculating the viscosity of a fluid held by the container wherein the container is sealed with a spherical ball held within the container as an integral package before the fluid is added thereto. The ball is formed to a specific desired density and to prevent shock during shipment which would cause the ball to break the container. Also the ball is formed to a size which facilitates detection.

A further object of the present invention is to provide a ball for a viscometer having a low density but an increased size to enhance sensing of the ball as it falls by gravity through a liquid.

Still another object of the present invention is to provide a viscometer for obtaining a measurement in situ wherein a spherical ball for measuring the viscoisty of a liquid within a container is raised from the bottom of the container magnetically so as not to disturb the liquid to be measured. A holder for the container includes a magnetic circuit to raise the ball along an inclined surface of the container.

A further object of the present invention is to provide a device for measuring the relative viscosity of the supernatant liquid remaining after centrifuging or settling of a fluid to separate suspended particles in the fluid. The device includes a spherical ball for measuring viscosity in situ, and structure is provided for holding the ball out of the liquid during settling or centrifugation. The device is further provided with structure to retain the ball while permitting suspended matter to pass and be separated from the active volume of liquid undergoing measurement.

Yet another object of the present invention is to provide a device for obtaining a measurement in situ which is useful for calculating the viscosity of a fluid including a sealed container, a rotating member located at the bottom of the container for providing rotary movement within the fluid wherein said rotating member includes a magnet, a magnetic power source located adjacent the rotating member for coupling magnetically therewith and a torque measuring instrument for measuring the amount of torque required to rotate the rotating member within the fluid at a range of constant speeds.

The above identified objects, as well as others, are achieved by an apparatus made in accordance with one embodiment of the present invention wherein a sealed container which may be evacuated to remove air therefrom includes a spherical ball to form an integral package before any fluid is placed within the container. The apparatus includes an angular support member which positions the container at an angle so that the ball will move within the container through the fluid at a specific speed. The support member includes a sensing device which is provided along the wall of the container to measure the speed of the ball wherein the sensing device includes a pair of sensors spaced apart by a known distance to sense when the ball passes by each of the sensors. Because the diameter and the density of the ball are known, the speed of the ball traveling through the fluid or down the wall of the container can be used to calculate the viscosity of the fluid held therein.

A second embodiment of the present invention provides a magnetic rotating member located within a container which is adaptable to a power source wherein a magnet included therewith couples with the magnetic rotating member to cause rotation of the rotating member. The device of the second embodiment further includes a torque measuring device which measures the amount of torque required to rotate the rotating member at a specified speed in the fluid. From these measurements at a number of constant speeds, the viscosity of the fluid can be calculated. In both of the embodiments, the viscosity can be determined without obtaining a sample of the fluid and thus, without disturbing the fluid in the container. This becomes very important for running chemical reactions over a period of time during which the progress of a chemical reaction is ascertained. Moreover, the apparatus of the present invention is also important for use with fluids which must be sealed from contaminants or foreign particles, such as blood.

BRIEF DESCRIPTION OF THE DRAWINGS

FIG. 7 is a side perspective view of a second embodiment of the container of the present invention; and FIG. 8 is a third embodiment of the container of the present invention.

DETAILED DESCRIPTION OF THE PREFERRED EMBODIMENT

Figure 1:
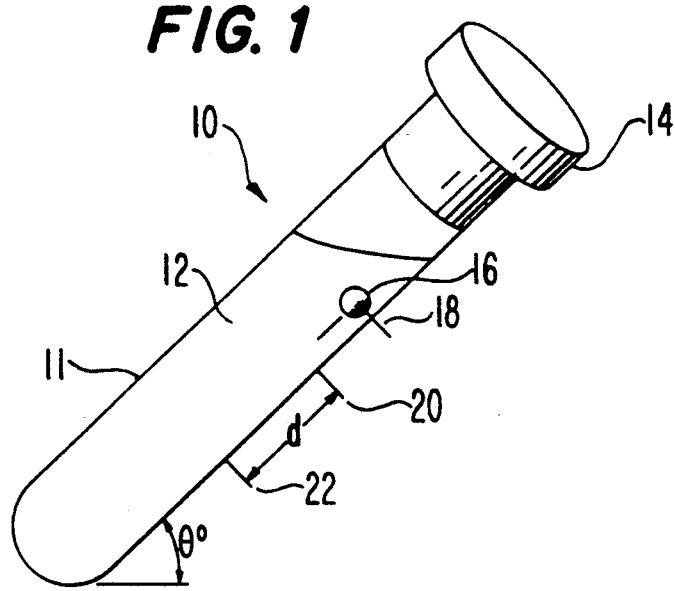
FIG. 1 is a side perspective view of the container made in accordance with the present invention.

Referring initially to FIG. 1, the container 10 of the present invention may be any number of types of vessels, such as a test tube, an Erlenmeyer flask, a beaker, or laboratory bottle, and such containers are normally formed of glass or other breakable material. In FIG. 1, container 10 is shown as a test tube 11 for holding a fluid 12. A container closure, illustrated as a stopper 14, is located at the open end of test tube 11 for protecting fluid 12 from the atmosphere. Although a stopper is shown for illustrative purposes, the container may be permanently closed air tight by a closure which is not intended for removal and which is pierced by a sterile needle or similar device for inserting fluid 12 into the container. This type of closure may be particularly useful for blood measurements.

The container 10 of the present invention includes a spherical ball 16 placed within the container prior to the reception of fluid 12 therein. Preferably, spherical ball 16 is packaged with container 10 to form an integral unit and to conveniently allow the container to be equipped for determining the viscosity of a fluid contained therein. Therefore, spherical ball 16 can be placed within container 10 at the factory and the container with ball can then be evacuated, sealed, sterilized and shipped as an integral unit.

Container 10 may be of any diameter or length, limited only by the constraints imposed for collecting a specified fluid 12. Moreover, spherical ball 16 could be constructed of any material, such as plastic, glass, or metal, that is substantially inert to the fluid held within container 10 and having an absolute density larger than the density of the fluid. However, because the spherical ball 16 is often shipped with glass or frangible containers, container 10 could be shattered during shipping due to the weight of the ball. The bottom of the container is most vulnerable to breakage during shipment. This is especially true when the ball must have a diameter which is large enough to be easily sensed by sensors, discussed in more detail below. If the spherical ball 16 is constructed small enough to reduce the possibility of damage to the container during shipping, the ball will be difficult to sense with conventional sensing devices and will wander as it travels through fluid 12 past the sensors.

Moreover, the Stokes equations set forth in the Background section, require the spherical ball 16 to reach its translational velocity before it moves into the predetermined distance d in FIG. 1. The diameter required for the spherical ball is greatly affected by the density of the material required to form it, and this material is determined by the density of the fluid to be measured. If a metallic ball with density considerably larger than the density of the fluid 12 is used and if the viscosity of the fluid 12 is in the range of water or even 100 times greater than water, the ball must be sufficiently small to reach its terminal translational velocity within the limited dimensions of container 10. The limited dimensions of a laboratory container often make it difficult to accurately detect displacement of a spherical ball 16 held within the container, since for some fluids, the ball would be tiny.

Figure 2:
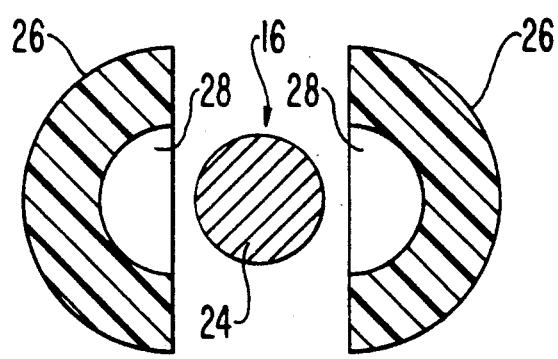
FIG. 2 is a cross sectional view of one embodiment of the composite spherical ball made in accordance with the present invention.

In accordance with the present invention, the diameter of spherical ball 16 may be increased so that sensors can more readily detect its displacement within container 10. Also, the ball of the present invention can be provided as an integral unit with a frangible laboratory container without causing damage to the container during shipping. Specifically, a composite spherical ball 16 includes a core 24 which may be made from a metallic material or another suitable material having a density which exceeds that of the fluid to be measured. The core is formed to a size and weight determined by the size and configuration of the container. In a small volume test tube container of the type shown at 10 in FIG. 1, the ball 16, if formed from a heavy, dense material such as metal, would be required to be tiny if it is to reach its translational velocity v before entering the measurement area between points 20 and 22. In FIG. 1, point 18 represents the ball drop point. This point establishes the distance required for the spherical ball 16 to reach its translational velocity, v described in the Background section. The distance d represents the measuring distance to determine the velocity of spherical ball 16 as is travels down the wall of test tube 11. As described in greater detail below, sensors are preferably placed at points 20 and 22 to accurately sense when spherical ball 16 passes each of the sensors to determine speed. The weight of core 24 will allow spherical ball 16 to reach its translational velocity within the confines of container 10. Half-spheres 26 are formed around the core 24 and are made of material having a much lower density than that of the core material. This lower density outer structure provides two important functions, namely, it is preferably made of low density shock absorbent material which protects container 10 during shipping, and it causes spherical ball 16 to have a sufficiently large diameter to be easily detected by conventional sensors during fluid testing. The embodiment illustrated in FIG. 2 shows the use of a plastic material for the half spheres 26, but however, any suitable light, shock resistant material may be used. The material would be limited to those materials which are inert to the fluid held within the given container.

Each half-sphere 26 is provided with a cut-out region 28 adapted to receive the core 24. A conventional adhesive or other bonding method can then be used to bind the half-spheres together around the core 24 before the ball 16 is sealed within the container 10.

Figure 3:
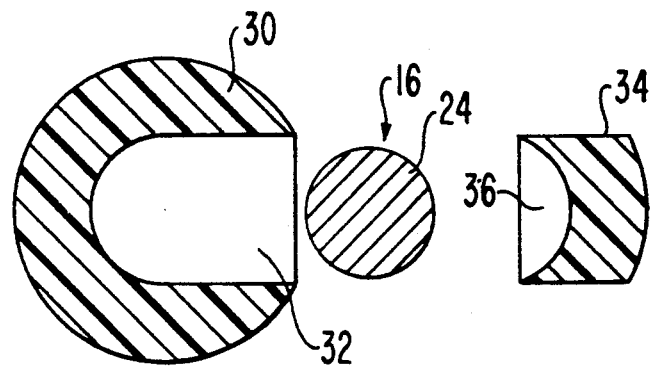
FIG. 3 is a cross sectional view of a second embodiment of the composite spherical ball made in accordance with the present invention.

FIG. 3 provides a second embodiment of spherical ball 16 wherein a small core 24' may also be made of a dense, heavy material. A hollow sphere 30 is provided with a slot 32 to allow core 24' to be slidable therein. Again, sphere 30 is shown made of a plastic material, but any material which is inert to the fluid 12 being tested would be acceptable. Slot 32 has a cross-sectional area slightly greater than the diameter of core 24' to facilitate insertion, and a plug 34 is provided to secure core 24' within sphere 30 to provide a composite spherical ball 16 having an increased diameter. Moreover, plug 34 is provided with an arcuate cutout portion 36 to allow adequate support of core 24' along its surface. Again, a conventional adhesive can be used to secure plug 34 within slot 32.

The embodiments illustrated in FIGS. 2 and 3 can be reversed under certain circumstances. A less dense material having a desired diameter may be coated with denser material, such as a metallic material, if the metallic components of a metallically composed spherical ball is desired. Some shock absorption characteristics may be lost with this coated structure, but often the coating is thin and flexible enough that shock absorption is still provided.

The container 10 of FIG. 1 provided with the composite ball of FIGS. 2 and 3 facilitates the shipment and use of a small laboratory container for in situ viscosity measurements. The shock absorbent characteristics of the composite ball not only permit the container with the ball to be safely shipped, but also permit the container with the ball to be centrifuged, shaken or otherwise somewhat violently manipulated in a laboratory to treat the liquid in the container without the likelihood of the ball causing damage to the container. Since the container and ball can be sterilized and sealed before shipment, fluid to be measured can be injected through the closure 14 for testing, and viscosity measurements can be taken in situ during testing. There is no need to pour fluid from a larger container into a separate viscosity measuring device as is the case with conventional viscosity measuring units. Thus a viscosity measurement can be rapidly taken using the container 10 of FIG. 1 without the chance of fluid contamination and without creating fluid disturbances which might either affect or delay the viscosity measuring process.

Often when a fluid in a laboratory container is being processed, it is desirable to take a viscosity measurement at different points in the process. The fact that the laboratory vessel contains the viscosity measuring ball permits a viscosity measurement to be rapidly taken with a minimum interruption to the process. For some processes, such as one where blood is separated into a plasma and a cellular fraction within the vessel, it is important to be able to take the viscosity measurement without remixing the components in the vessel more than is necessary. If the vessel is inverted to raise the ball to the top of the vessel, excessive mixing of the fluid will occur.

Figure 4:
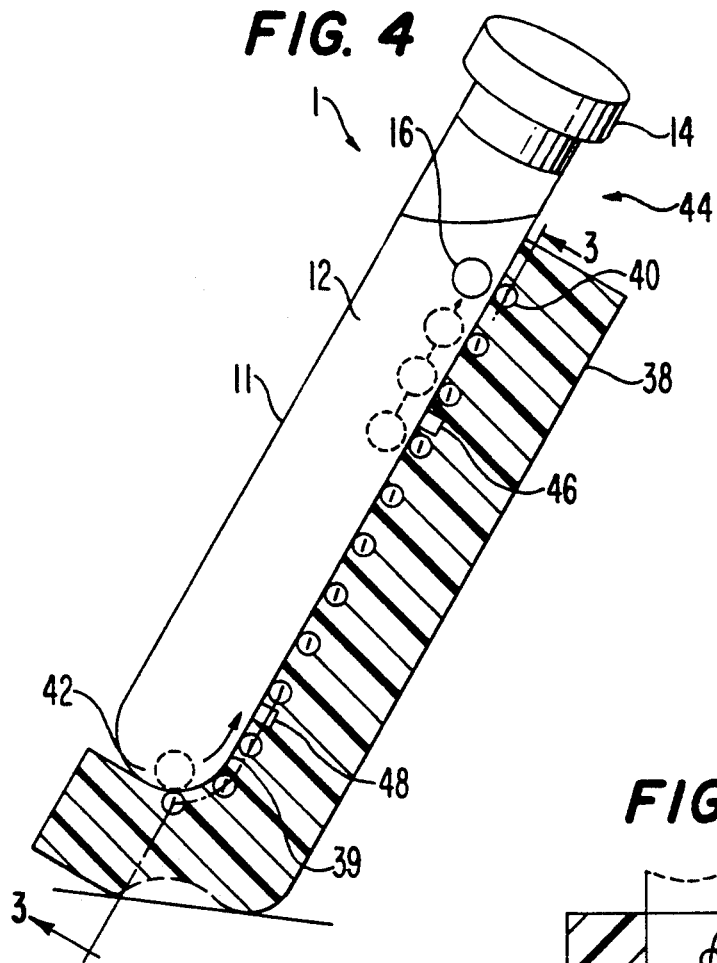
FIG. 4 is a partial cut-away side view of the container and the angular support made in accordance with the present invention.

FIG. 4 illustrates a measuring support member for use with the container 10 which will provide a viscosity measurement while minimizing any disturbance of the fluid within the container.

The test tube 11 is held at an angle θ° by angular support member 38 to avoid the problems associated with the inversion of test tube 11. Specifically, angular support member 38 is shaped to accommodate the particular container 10. A curved support surface 39 is provided to adequately support the bottom and an arcuate section of the sidewall of the test tube 11. Although angular support member 38 may be fabricated from any conventional material, it is preferably constructed of a plastic material such as Plexiglas. Spaced electromagnets 40 are mounted within the angular support member 38 and extend along the support surface 39 thereof to contact the outer surface of test tube 11.

Figure 5:
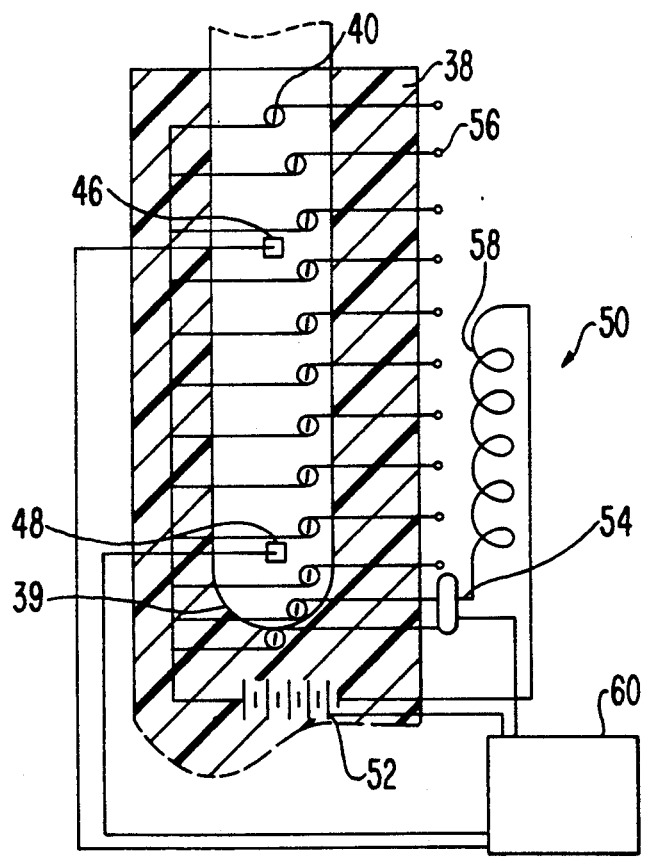
FIG. 5 is a partial cut-away side view taken along line 3—3 of FIG. 4.

FIG. 5 shows the electric circuit 50 for the angular support member 38. This electric circuit includes the electromagnets 40 which create a ladder running vertically upward from the bottom of the support member to a point adjacent the top. The top electromagnet will be positioned at the drop point for the spherical ball 16. Moreover, the electromagnets 40 run in an arcuate path to avoid sensors 46 and 48 which are mounted in the support member 38 so as to contact the wall of the container 10. The sensors are placed at a known distance apart to determine the speed of spherical ball 16 as it travels down the wall of test tube 11. These sensors are not limited to photoelectric sensors, but may be magnetic, capacitance, inductance or other suitable sensors as long as they are capable of detecting the displacement of spherical ball 16. A power source 52 is provided on one support member 38 and is connectable in parallel to electromagnets 40. The circuit to each electromagnet 40 from the power sources is sequentially completed by a slide switch 54 contacting a connector 56 of each electromagnet. Slide switch 54 is shown as a manually operated switch, but the switch may be motor driven to automatically provide sequential energization to each of the electromagnets 40. A flexible cable 58 is provided to allow freedom of movement along the side of angular support member 38.

Figure 6:
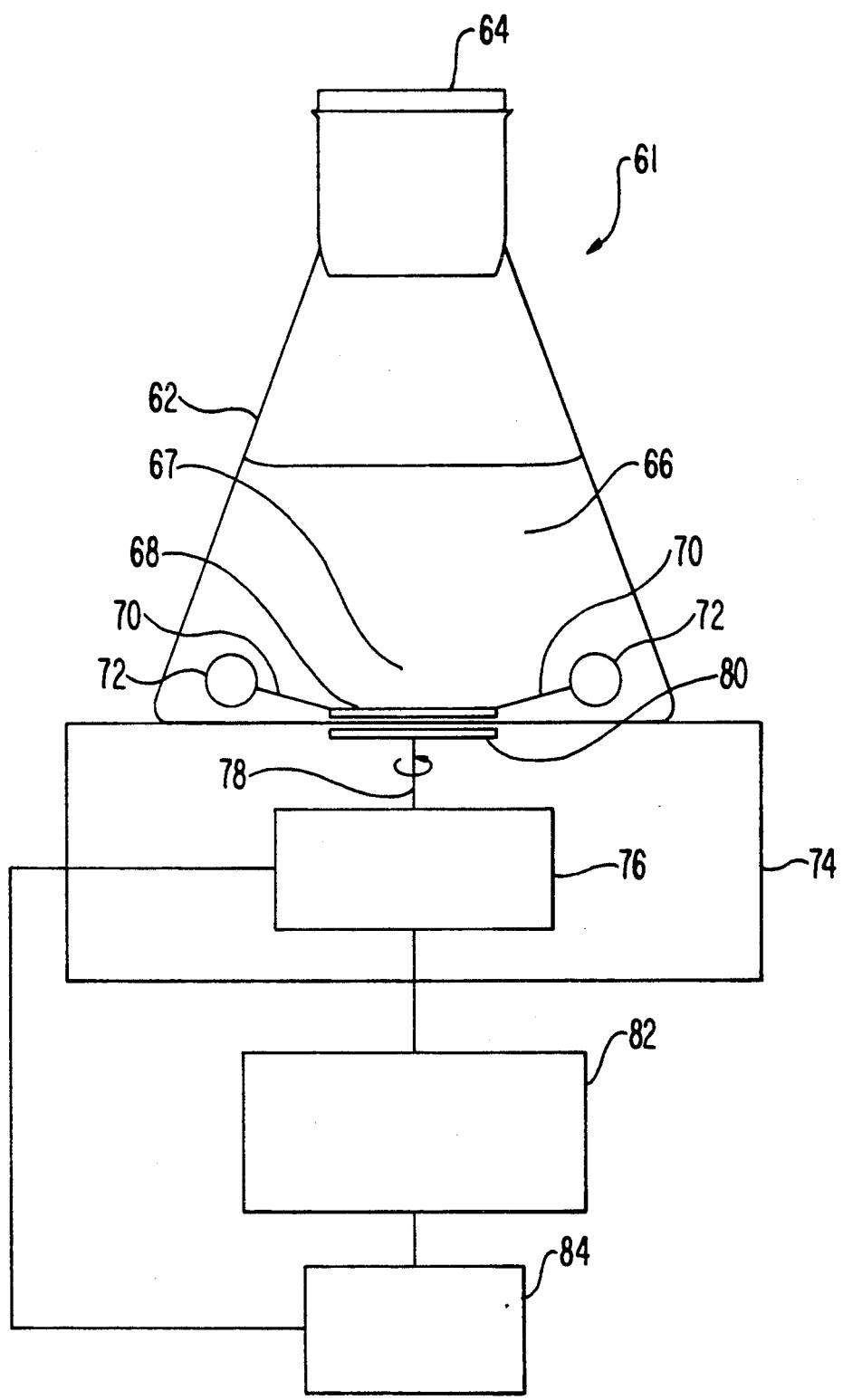
FIG. 6 is a general schematic diagram of a second embodiment of the present invention.

As referred to above, the concept of measuring the viscosity of a fluid held within a container without requiring the drawing of a sample may be accomplished in a variety of ways. The embodiment of FIG. 6 illustrates a second device 61 for determining the viscosity of a fluid which does not require the inversion of the container and allows a viscosity sensitive member to be present within the container during shipping. Specifically, an Erlenmeyer flask 62 is provided with a flask stopper 64 to seal fluid 66 from the atmosphere. Flask 62 is made to include a rotating member 67 which is located centrally within flask 62. Rotating member 67 is designed to be nonsymmetrical. It includes a permanent magnet 68 from which shafts 70 extend on opposite sides thereof. Weighted balls 72 are attached to each end of shafts 70 to complete the rotating member. The weighted balls may be substituted by paddles or the like depending upon the fluid tested.

Flask 62 is designed to rest upon platform 74. Platform 74 includes a DC shunt motor with speed reducer 76 which is equipped with a rotating shaft 78 to which a magnet 80 is attached. The rotation speed of the motor 76 as well as the rotating member 67 by means of the magnetic coupling between magnets 68 and 80 is controlled by adjusting the DC voltage to motor 76 from DC power supply 82. Finally, a microprocessor 84 may be connected to power supply 82 to calculate torque from the armature current maintained in motor 76 and for calculating the viscosity of fluid 66 using the torque and the rotational speed of the motor and speed reducer 76.

The concept of the present invention may be used in a variety of fields. One such area in which the simple design illustrated in FIG. 1 may be used is in the area of blood analysis. Whole blood and plasma viscosities are physical properties that are not routinely determined, yet these measurements help to indicate the state of patient health which may be valuable to health professionals. Use of the present invention would not interfere with other measurements for the same blood sample, such as for hemoglobin, electrolyte levels, etc. because no sample is required and the blood can remain free from contaminants.

The present invention provides spherical ball 16 to be placed into a blood-collecting tube before the tube is sterilized, sealed and evacuated. The method for determining viscosity is the well-known Stokes' law principle that the velocity of a sphere falling by gravity is inversely related to the viscosity. Referring to FIG. 1, the velocity of the falling or the elapsed time for spherical ball 16 to travel between point 20 and point 22, a known distance apart, d, along the length of test tube 11. Various methods to sense displacement of the ball between the two points can be used, such as visually, optical sensors, magnetic sensors or the like. The container 10 can be calibrated by measurements of elapsed time when operated with other reference liquids of known viscosity and the viscosity of the blood can then be calculated from the elapsed time, the distance between the two points, the absolute density of the blood and the ball and the diameter of the ball and the collecting tube. Because the density of the fluid may not be known, at least two spheres of known density can be used in the fluid. Each sphere can be made to fall or roll and the velocities obtained can be inserted into an equation such as equations (1), (2) or a calibration equation. These equations can be solved simultaneously to reach values for both the density and the relative viscosity of the fluid. Measurements can be made with the tube in a vertical position or inclined at any angle where the ball can freely roll. Repeat determinations by simply inverting the tube or by use of a magnet to manipulate spherical ball 16, constructed at least partly of magnetic materials, are also possible.

The operation of apparatus 1 shown in FIGS. 4 and 5 is very simple to perform. After the fluid has been introduced into test tube 11 which is properly sealed with stopper 14, power source 52 energizes slide switch 54 beginning at lower portion 42 to engage spherical ball 16. Successive connectors 56 are contacted as slide switch 54 moves vertically up angular support member 38, gradually raising spherical ball 16 to upper portion 44. When it has reached the drop point at upper portion 44, the uppermost electromagnet 40 is de-energized to release spherical ball 16 to allow it roll down the inner wall of test tube 11 and pass over sensors 46 and 48, successively. The time at which the ball passed sensors 46 and 48 is inputted to microprocessor 60 to determine the translational velocity, v, of spherical ball 16. Using this speed determination, microprocessor 60 can calculate the viscosity of the fluid. The apparatus may be initially calibrated using a fluid of known viscosity to set the appropriate parameters and constants used in the Stoke's equation discussed in the Background.

The operation of device 61, represented in FIG. 6, is based on similar principles. Again fluid 66 is introduced into flask 62 which has been presealed with flask stopper 64. When a viscosity measurement is desired, motor 76 which is mounted within a platform 74 is activated to cause a rotating shaft 78 to begin movement. A magnet 80 is secured to shaft 78 and magnetically coupled to a permanent magnet 68 for a rotating member 67 which will turn in relation to the torquing force provided by the motor 76. The rotating member is caused to rotate at a number of constant speeds and includes spherical balls 72 connected to magnet 68 by arms 70. The torque is calculated from the armature current provided by power supply 82 to the motor and speed reducer 76 required to cause the rotating member 67 to reach each constant speed. These measurements are input to microprocessor 84.

The viscosity of fluid 66 is calculated from the torque required for each constant speed by appropriate mathematical relations stored within microprocessor 94, or microprocessor 84 can be calibrated by measuring the torque and speed for a number of fluids of known viscosity and comparing those to the parameters input for fluid 66.

The balls 72 may be constructed in the same manner as the balls 16 previously described, and the rotating member 67 is shipped with the container 61.

The advantages of this embodiment, as well as the first embodiment described above, is avoiding the need to remove a sample of the fluid for measurement with conventional viscometers. Another advantage is to permit viscosity measurements in closed containers while avoiding a change of pressure caused by opening the container to the atmosphere or causing contamination of the fluid in the container. Moreover, because spherical ball 16 can be designed as a composite, these measurements may be accomplished in ordinary laboratory containers, and spherical ball 16 will have a sufficient diameter for displacement detection by conventional sensors while also protecting the container from damage during shipping. By providing containers with components prepackaged therein, viscosity measurements may be calculated more often for one particular fluid. Moreover, determining viscosity of the fluid within its original container will greatly decrease the possibility of agitating the fluid while transferring it from another container which may result in a false viscosity determinations.

Referring now to FIGS. 7 and 8, the tube 10 may be modified to provide a device for measuring the relative viscosity of a supernatant liquid which remains after centrifuging or settling of a fluid to separate suspended particles in the fluid. As shown by FIG. 7, a circular disc 86 including an open mesh 88 is spaced above the bottom of the container 10. This disc can be held in position by any known means, such as a rubber seal around the outer peripheral edge of the disc or by fingers or ridges formed in the glass inner surface of the container. The disc may also be positioned by three legs 90 extending from the disc at 120° intervals.

When liquid, such as blood, is contained in the container 10 of FIG. 7, it may be centrifuged in the container to separate the red blood cells. During centrifugation, test tubes are normally positioned at an angle of 33°–40° from the vertical, and the red blood cells would pass through the mesh 88 and be collected below the disc 86. Since the disc is formed to prevent the ball 16 from reaching the material below the disc, the ball may be used to obtain a viscosity measurement of the fluid remaining above the disc.

To prevent the ball 16 from becoming coated with a residue such as settled red blood cells within the container 10 during centrifugation, the container is formed with inwardly projecting fingers or ridges 92 which angle toward the closure 14. These projections may be formed from the glass used for the container wall and operate to cradle the spherical ball 16 above the liquid in the container and between the container wall and the projections during centrifugation. The ball may be raised magnetically and deposited in the space between the projections and the container wall as shown in FIGS. 7 and 8. After the centrifugation process is complete, the ball may be dislodged from the projections magnetically.

The test tube or container 10 may also be formed with spaced projecting fingers 94 to retain the ball 16 above the bottom of the container as illustrated in FIG. 8. These projecting fingers formed from the glass sidewall of the container may extend into the tube for a sufficient distance to preclude passage of the ball 16. However, particulate material or materials suspended in fluid, such as red blood cells, can fall between the fingers to the bottom of the container.

In some cases, the fingers 94 can be formed to project into the container 10 for only a small distance. To prevent the ball 16 from passing between the fingers, the disc 86 without the legs 90 would be inserted to rest upon the fingers.

The foregoing detailed description of the invention is considered exemplary in nature, and it should be appreciated by those skilled in the art that the invention may be practiced otherwise than as specifically described herein without departing from the spirit and scope of the invention. It is, therefore, to be understood that the spirit and scope of the invention be limited only by the following claims.

We claim:

1. An apparatus for measuring the viscosity of a fluid in situ comprising:
   (a) a sealed, frangible container for holding said fluid including an inlet portion and a base portion; and
   (b) a composite ball having a known diameter and density enclosed within said container, said composite ball including an outer shell portion and an interior core portion enclosed by said outer shell portion, one of said outer shell portion or interior core portion being formed of a first material and the remaining shell portion or interior core portion being formed of a second material which differs from said first material, said first material having a substantially different density than said second material, said second material operating to diametrically increase the size of said composite ball.

2. An apparatus of claim 1, wherein the outer shell portion is formed from said second material, said second material being a shock absorbing material which absorbs sufficient shock to prevent breakage of said container.

3. An apparatus as set forth in claim 2, further including an angular support means for supporting said container at a predetermined angle to cause a displacement of said composite ball within said container.

4. An apparatus as set forth in claim 3, wherein said interior core portion is formed from a metallic material and said angular support means includes a magnetic means mounted within said angular support means, said magnetic support means operative for magnetically manipulating said composite ball.

5. An apparatus as set forth in claim 4, wherein said magnetic means includes a plurality of spaced electromagnets connected in parallel to a common power extend adjacent to said container from said inlet so as to said base portion when said container is disposed on said angular support means.

6. An apparatus as set forth in claim 3, further including sensor means located intermediate of said inlet and said base portion of said container for detecting said displacement of said composite ball.

7. An apparatus as set forth in claim 6, wherein said sensor means includes a pair of photoelectric sensors spaced apart by a known distance to provide an output indicative of a time measurement for calculating the velocity of said composite ball during said displacement.

8. An apparatus as set forth in claim 7, further including a processor means for monitoring said sensor means to receive said output.

9. A container for measuring the viscosity in situ of a fluid contained therein comprising a frangible body means defining an enclosed central chamber, an inlet opening into said chamber, closure means closing and sealing said inlet opening, and a ball held within said chamber as an integral package by said sealed closure means before said fluid is added to said container, said chamber containing said ball being evacuated and sterilized.

10. A container as set forth in claim 9, wherein said ball is formed of shock absorbing material to guard against breakage of said container during shipment.

11. A container as set forth in claim 10, wherein said ball includes an interior core portion formed from a metallic material which allows magnetic manipulation thereof.

12. A container as set forth in claim 9, wherein said ball is a composite ball present within said container before said closure means is affixed to said inlet opening, said ball being formed of at least two materials of different densities.

13. A container as set forth in claim 9, wherein said closure means is formed from a penetrable material to allow penetration thereof with a sterile needle for injection of said fluid into said container.

14. A container as set forth in claim 9, further including a retaining means located near said inlet opening for retaining said ball within said central cavity above said fluid held within said container.

15. A container as set forth in claim 14, further including a separation means located near the bottom of said container within said central cavity for separating said ball from settled components of said fluid located below said separation means.

16. A composite ball for insertion into a viscosity measuring unit for measuring the viscosity of a fluid comprising:
(a) an outer shell portion;
(b) an interior core portion enclosed by said outer shell portion;
(c) said interior core portion being formed of a first material; and
(d) the outer shell portion being formed of a second material which differs from said first material, said first material having a substantially greater density and weight than said second material, said second material being formed to diametrically increase the size of said composite ball, and said outer shell portion including a sphere and a plug formed from said second material wherein said sphere is formed to include a slot for receiving said interior core portion and said plug is designed to be insertable within said slot to completely encase said interior core portion.

* * * * *